United States Patent
Delaney, Jr. et al.

(10) Patent No.: US 11,185,615 B2
(45) Date of Patent: Nov. 30, 2021

(54) PET SOLUTIONS AND METHODS OF MAKING PET SOLUTIONS FOR MEDICAL DEVICES

(71) Applicant: Cardiac Pacemakers, Inc., St. Paul, MN (US)

(72) Inventors: Joseph T. Delaney, Jr., Minneapolis, MN (US); David R. Wulfman, Minneapolis, MN (US); Adeniyi O. Aremu, Brooklyn Park, MN (US); Adegbola O. Adenusi, Burnsville, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 0 days.

(21) Appl. No.: 16/598,402

(22) Filed: Oct. 10, 2019

(65) Prior Publication Data
US 2020/0038561 A1   Feb. 6, 2020

Related U.S. Application Data

(62) Division of application No. 15/485,491, filed on Apr. 12, 2017, now Pat. No. 10,441,688.

(60) Provisional application No. 62/321,726, filed on Apr. 12, 2016.

(51) Int. Cl.

| | | |
|---|---|---|
| A61L 31/10 | (2006.01) | |
| D01D 1/02 | (2006.01) | |
| C08G 63/183 | (2006.01) | |
| A61L 27/34 | (2006.01) | |
| D01D 5/00 | (2006.01) | |
| D01F 6/62 | (2006.01) | |
| C09D 7/20 | (2018.01) | |
| B05D 1/04 | (2006.01) | |
| B05D 3/04 | (2006.01) | |
| C08L 67/02 | (2006.01) | |
| C09D 167/02 | (2006.01) | |

(52) U.S. Cl.
CPC .............. *A61L 31/10* (2013.01); *A61L 27/34* (2013.01); *B05D 1/04* (2013.01); *B05D 3/04* (2013.01); *C08G 63/183* (2013.01); *C08L 67/02* (2013.01); *C09D 7/20* (2018.01); *C09D 167/02* (2013.01); *D01D 1/02* (2013.01); *D01D 5/003* (2013.01); *D01D 5/0084* (2013.01); *D01F 6/62* (2013.01); *A61L 2420/02* (2013.01)

(58) Field of Classification Search
CPC .... D01F 6/62; A61L 31/10; C09K 8/72; C09J 5/12; D01D 1/02; C08G 63/183
See application file for complete search history.

(56) References Cited

U.S. PATENT DOCUMENTS

| | | | |
|---|---|---|---|
| 9,668,742 B2 * | 6/2017 | Blum | A61B 17/12109 |
| 10,441,688 B2 | 10/2019 | Delaney et al. | |
| 2008/0119374 A1 | 5/2008 | Willberg et al. | |
| 2008/0247987 A1 * | 10/2008 | Liggins | A61K 47/34 424/78.17 |
| 2013/0291878 A1 * | 11/2013 | Takayama | A41D 13/1192 128/863 |
| 2015/0257763 A1 | 9/2015 | Blum et al. | |
| 2017/0290957 A1 | 10/2017 | Delaney et al. | |

OTHER PUBLICATIONS

Hansen, Charles M. Hansen Solubility Parameters: A User's Handbook, 2nd ed. New York, CRC Press, Taylor & Francis Group, 2007, 546 pages.
International Search Report and Written Opinion issued in PCT/US2017/027119, dated Jul. 14, 2017, 12 pages.
Ke, Huizhen. "Electrospun Form-Stable Phase Change Composite Nanofibers Consisting of Capric Acid-based Binary Fatty Acid Eutectics and Polyethylene Terephthalate." Fibers and Polymers, 14(1):89-99, 2013.
Mahalingam, Suntharavathanan, et. al. "Solubility-Spinnability Map and Model for the Preparation of Fibres of Polyethylene (Terephthalate) Using Gyration and Pressure." Chemical Engineering Journal, 280:344-353, 2015.

* cited by examiner

*Primary Examiner* — Dah-Wei D. Yuan
*Assistant Examiner* — Andrew J Bowman
(74) *Attorney, Agent, or Firm* — Faegre Drinker Biddle & Reath LLP

(57) ABSTRACT

A method of making a solution including poly(ethylene terephthalate). The method includes dissolving poly(ethylene terephthalate) in a solvent mixture to form a solution, the solvent mixture including two solvent components. A Hansen Solubility Parameter Distance between the solvent mixture and HSP coordinates having a dispersion HSP of 18.02 $MPa^{0.5}$, a polar HSP of 5.56 $MPa^{0.5}$, and a hydrogen bonding HSP of 14.27 $MPa^{0.5}$ is less than about 2 $MPa^{0.5}$.

18 Claims, No Drawings

PET SOLUTIONS AND METHODS OF MAKING PET SOLUTIONS FOR MEDICAL DEVICES

CROSS-REFERENCE TO RELATED APPLICATION

This application is a division of U.S. application Ser. No. 15/485,491, filed Apr. 12, 2017, which claims priority to Provisional Application No. 62/321,726, filed Apr. 12, 2016, which is herein incorporated by reference in its entirety.

TECHNICAL FIELD

The present invention relates to solutions and methods for making solutions of polymers suitable for solvent-based polymer processing. More specifically, the invention relates to solutions containing poly(ethylene terephthalate) and methods for making solutions containing poly(ethylene terephthalate).

BACKGROUND

Polymeric materials are widely used in the field of implantable medical devices. Poly(ethylene terephthalate) (PET) in particular is widely used for implantable medical devices such as catheters, electrical lead bodies, surgical mesh, implantable sutures, vascular grafts, tissue scaffolds, tracheal tubes, and esophageal stents. PET has a long history of biostability and is one of only a few polymers approved for long term implant use in medical devices.

Incorporating PET into implantable medical devices may be done by a variety of methods, depending on the specific application. In some applications, PET may be extruded at a temperature sufficient to cause the PET to flow, but not high enough to cause the PET to break down. That is, the PET material forming the medical device after the extrusion and cooling has largely the same structure as the original PET material.

In other applications, it may be desirable to employ solvent-based processing to incorporate polymeric materials, such as PET, into an implantable medical device. Solvent-based processing includes electrospraying, electrospinning, spray coating, dip coating, and force spinning. Essential to all solvent-based processing of polymeric materials is the ability to bring the polymeric material into solution while retaining the basic structure of the polymeric material. In some cases, solutions of polymeric materials may be limited to only a few weight percent of the polymeric material (e.g. less than about 2 wt. %). Solutions having such low weight percent of polymeric material dissolved may not be economically useful in some solvent-base processing, and may not work at all in other solvent-based processing. In still other cases, it may be possible to bring a polymeric material into solution at adequate concentrations, but the solvent may be so acutely hazardous to humans or the environment that its use is undesirable.

SUMMARY

Example 1 is a method of making a solution including poly(ethylene terephthalate). The method includes dissolving poly(ethylene terephthalate) in a solvent mixture to form a solution, the solvent mixture including two solvent components. A Hansen Solubility Parameter Distance between the solvent mixture and HSP coordinates having a dispersion HSP of 18.02 $MPa^{0.5}$, a polar HSP of 5.56 $MPa^{0.5}$, and a hydrogen bonding HSP of 14.27 $MPa^{0.5}$ is less than about 2 $MPa^{0.5}$.

In Example 2, the method of Example 1, wherein the solvent mixture consists of two solvent components, a first solvent component and a second solvent component, wherein the first solvent component is present in the solvent mixture in concentrations of greater than or equal to about 50 vol. % of the solvent mixture, with the balance being the second solvent component In Example 3, the method of Example 2, wherein the first solvent component is cinnamyl alcohol and the second solvent component is 2-methyl-1,3-butanediol, 1-butanol, 2-propanol, or 3-methyl allyl alcohol; the first solvent component is 2-phenoxy ethanol and the second solvent component is thymol; or the first solvent component is n-butyl salicylate and the second solvent component is ethylene glycol.

In Example 4, the method of Example 2, wherein the second solvent component is dl-lactic acid and the first solvent component is one of (E)-cinnamyl alcohol, 2-allylphenol, 4-propylphenol, chavicol, dihydroeugenol, hawthorn carbinol, hawthorn ethanol, isopropenylphenol, n-butyl salicylate, peony alcohol, and trans anethole.

In Example 5, the method of Example 2, wherein the first solvent component is benzyl alcohol and the second solvent component is one of 1-butanol, iso-butanol, and ethylene glycol.

In Example 6, the method of Example 2, wherein the first solvent component is thymol and the second solvent component is one of 2,3-butanediol, 2-hydroxy-2-methylpropanoic acid, and 2-methyl-1,3-butanediol.

In Example 7, the method of any of Examples 1-6, wherein at least one of the first solvent component and the second solvent component has a Hansen polar solubility parameter of at least about 5.6 $MPa^{0.5}$, and a Hansen hydrogen bonding parameter of at least about 4.6 $MPa^{0.5}$.

In Example 8, the method of any of Examples 1-7, wherein the solubility of the poly(ethylene terephthalate) in the solvent mixture is at least about 2 wt. % at a temperature from about 20° C. to about 25° C.

Example 9 is a method for making an implantable medical device including a poly(ethylene terephthalate) layer. The method includes formulating a poly(ethylene terephthalate) solution according to any of Examples 1-8, depositing the poly(ethylene terephthalate) solution onto the implantable medical device, and drying the implantable medical device and evaporating the solvent mixture to leave behind the poly(ethylene terephthalate) layer.

In Example 10, the method of Example 9, wherein depositing includes at least one of electrospinning and electrospraying the poly(ethylene terephthalate) solution onto the implantable medical device.

Example 11 is a composition including a first solvent, a second solvent, and poly(ethylene terephthalate) in solution with the first solvent and the second solvent in an amount no less than about 2 wt. %. A Hansen Solubility Parameter Distance between the solvent mixture and HSP coordinates has a dispersion HSP of 18.02 $MPa^{0.5}$, a polar HSP of 5.56 $MPa^{0.5}$, and a hydrogen bonding HSP of 14.27 $MPa^{0.5}$ is less than about 2 $MPa^{0.5}$.

In Example 12, the composition of Example 11, wherein the first solvent of the composition is (E)-cinnamyl alcohol and the second solvent is dl-lactic acid; the first solvent is 2-phenoxy ethanol and the second solvent is thymol; the first solvent is 2-allylphenol and the second solvent is dl-lactic acid; the first solvent cis 4-propylphenol and the second is dl-lactic acid; the first solvent is trans anethole and the second solvent is dl-lactic acid; the first solvent is benzyl alcohol and the second solvent is ethylene glycol, iso-butanol, or 1-butanol; the first solvent is chavicol and the second solvent is dl-lactic acid; the first solvent is cinnamyl alcohol and the second solvent is 2-methyl-1,3-butanediol, 1-butanol, 2-propanol, or 3-methyl allyl alcohol; the first solvent is dihydroeugenol and the second solvent is dl-lactic acid; the first solvent is hawthorn carbinol, and the second solvent is dl-lactic acid; the first solvent is hawthorn ethanol and the second solvent is dl-lactic acid; the first solvent is isopropenylphenol and the second solvent is dl-lactic acid; the first solvent is n-butyl salicylate and the second solvent is dl-lactic acid or ethylene glycol; the first solvent is peony alcohol and the second solvent is dl-lactic acid; or the first solvent is thymol and the second solvent is 2,3-butanediol, 2-methyl-1,3-butanediol, or 2-hydroxy-2-methylpropanoic acid.

In Example 13, the composition of Example 12, wherein the second solvent is dl-lactic acid and the first solvent is one of (E)-cinnamyl alcohol, 2-allylphenol, 4-propylphenol, chavicol, dihydroeugenol, hawthorn carbinol, hawthorn ethanol, isopropenylphenol, n-butyl salicylate, peony alcohol, and trans anethole.

In Example 14, the composition of any of Examples 11-13, wherein at least one of the first solvent and the second solvent has a Hansen polar solubility parameter of at least about 5.6 $MPa^{0.5}$, and a Hansen hydrogen bonding parameter of at least about 4.6 $MPa^{0.5}$.

In Example 15, the composition of any of Examples 11-14, wherein poly(ethylene terephthalate) is in solution with the first solvent and the second solvent in an amount no less than about 10 wt. %.

Example 16 is a method of making a solution including poly(ethylene terephthalate). The method includes dissolving poly(ethylene terephthalate) in a solvent mixture to form a solution, the solvent mixture including at least two solvent components. A solubility of the poly(ethylene terephthalate) in the solvent mixture is at least about 2 wt. % at a temperature from about 20° C. to about 25° C. A Hansen Solubility Parameter Distance between the solvent mixture and HSP coordinates having a dispersion HSP of 18.02 $MPa^{0.5}$, a polar HSP of 5.56 $MPa^{0.5}$, and a hydrogen bonding HSP of 14.27 $MPa^{0.5}$ is less than about 2 $MPa^{0.5}$.

In Example 17, the method of Example 16, wherein the solvent mixture consists of two solvent components, a first solvent component and a second solvent component, wherein the first solvent component is present in the solvent mixture in concentrations of greater than or equal to about 50 vol. % of the solvent mixture, with the balance being the second solvent component In Example 18, the method of Example 17, wherein the second solvent component is dl-lactic acid and the first solvent component is one of (E)-cinnamyl alcohol, 2-allylphenol, 4-propylphenol, chavicol, dihydroeugenol, hawthorn carbinol, hawthorn ethanol, isopropenylphenol, n-butyl salicylate, peony alcohol, and trans anethole.

In Example 19, the method of Example 17, wherein the first solvent component is 2-phenoxy ethanol and the second solvent component is thymol; or the first solvent component is n-butyl salicylate and the second solvent component is ethylene glycol.

In Example 20, the method of Example 17, wherein the first solvent component is benzyl alcohol and the second solvent component is one of 1-butanol, iso-butanol, and ethylene glycol.

In Example 21, the method of Example 17, wherein the first solvent component is thymol and the second solvent component is one of 2,3-butanediol, 2-hydroxy-2-methylpropanoic acid, and 2-methyl-1,3-butanediol.

In Example 22, the method of Example 17, wherein the first solvent component is cinnamyl alcohol and the second solvent component is one of 2-methyl-1,3-butanediol, 1-butanol, 2-propanol, or 3-methyl allyl alcohol.

In Example 23, the method of any of Examples 17-22, wherein at least one of the first solvent component and the second solvent component has a Hansen polar solubility parameter of at least about 5.6 $MPa^{0.5}$, and a Hansen hydrogen bonding parameter of at least about 4.6 $MPa^{0.5}$.

In Example 24, the method of any of Examples 16-23, wherein the solubility of the poly(ethylene terephthalate) in the solvent mixture is at least about 10 wt. % at a temperature from about 20° C. to about 25° C.

Example 25 is a method for making an implantable medical device including a poly(ethylene terephthalate) layer. The method includes formulating a poly(ethylene terephthalate) solution by dissolving poly(ethylene terephthalate) in a solvent mixture to form a solution, depositing the poly(ethylene terephthalate) solution onto the implantable medical device, and drying the implantable medical device and evaporating the solvent mixture to leave behind the poly(ethylene terephthalate) layer. The solvent mixture includes at least two solvent components. A solubility of the poly(ethylene terephthalate) in the solvent mixture is at least about 2 wt. % at a temperature from about 20° C. to about 25° C. A Hansen Solubility Parameter Distance between the solvent mixture and HSP coordinates having a dispersion HSP of 18.02 $MPa^{0.5}$, a polar HSP of 5.56 $MPa^{0.5}$, and a hydrogen bonding HSP of 14.27 $MPa^{0.5}$ is less than about 2 $MPa^{0.5}$.

In Example 26, the method of Example 25, wherein the solvent mixture consists of two solvent components, a first solvent component and a second solvent component, wherein the first solvent component is present in the solvent mixture in concentrations of greater than or equal to about 50 vol. % of the solvent mixture, with the balance being the second solvent component.

In Example 27, the method of Example 26, wherein the first solvent component of the composition is (E)-cinnamyl alcohol and the second solvent component is dl-lactic acid; the first solvent component is 2-phenoxy ethanol and the second solvent component is thymol; the first solvent component is 2-allylphenol and the second solvent component is dl-lactic acid; the first solvent component cis 4-propylphenol and the second is dl-lactic acid; the first solvent component is trans anethole and the second solvent component is dl-lactic acid; the first solvent component is benzyl alcohol and the second solvent component is ethylene glycol, iso-butanol, or 1-butanol; the first solvent component is chavicol and the second solvent component is dl-lactic acid; the first solvent component is cinnamyl alcohol and the second solvent component is 2-methyl-1,3-butanediol, 1-butanol, 2-propanol, or 3-methyl allyl alcohol; the first solvent component is dihydroeugenol and the second solvent component is dl-lactic acid; the first solvent component is hawthorn carbinol, and the second solvent component is dl-lactic acid; the first solvent component is hawthorn ethanol and the second solvent component is dl-lactic acid; the first solvent component is isopropenylphenol and the second solvent component is dl-lactic acid; the first solvent component is n-butyl salicylate and the second solvent component is dl-lactic acid or ethylene glycol; the first solvent component is peony alcohol and the second solvent component is dl-lactic acid; or the first solvent component is thymol and the second solvent component is 2,3-butanediol, 2-methyl-1,3-butanediol, or 2-hydroxy-2-methylpropanoic acid.

In Example 28, the method of either of Examples 26 or 27, wherein at least one of the first solvent component and the second solvent component has a Hansen polar solubility parameter of at least about 5.6 MPa$^{0.5}$, and a Hansen hydrogen bonding parameter of at least about 4.6 MPa$^{0.5}$.

In Example 29, the method of any of Examples 25-28, wherein the solubility of the poly(ethylene terephthalate) in the solvent mixture is at least about 10 wt. % at a temperature from about 20° C. to about 25° C.

In Example 30, the method of any of Examples 25-29, wherein depositing includes at least one of electrospinning and electrospraying the poly(ethylene terephthalate) solution onto the implantable medical device.

Example 31 is a composition including a first solvent, a second solvent, and poly(ethylene terephthalate) in solution with the first solvent and the second solvent in an amount no less than about 2 wt. %. A Hansen Solubility Parameter Distance between the solvent mixture and HSP coordinates having a dispersion HSP of 18.02 MPa$^{0.5}$, a polar HSP of 5.56 MPa$^{0.5}$, and a hydrogen bonding HSP of 14.27 MPa$^{0.5}$ is less than about 2 MPa$^{0.5}$.

In Example 32, the composition of Example 31, wherein the first solvent of the composition is (E)-cinnamyl alcohol and the second solvent is dl-lactic acid; the first solvent is 2-phenoxy ethanol and the second solvent is thymol; the first solvent is 2-allylphenol and the second solvent is dl-lactic acid; the first solvent cis 4-propylphenol and the second is dl-lactic acid; the first solvent is trans anethole and the second solvent is dl-lactic acid; the first solvent is benzyl alcohol and the second solvent is ethylene glycol, isobutanol, or 1-butanol; the first solvent is chavicol and the second solvent is dl-lactic acid; the first solvent is cinnamyl alcohol and the second solvent is 2-methyl-1,3-butanediol, 1-butanol, 2-propanol, or 3-methyl allyl alcohol; the first solvent is dihydroeugenol and the second solvent is dl-lactic acid; the first solvent is hawthorn carbinol, and the second solvent is dl-lactic acid; the first solvent is hawthorn ethanol and the second solvent is dl-lactic acid; the first solvent is isopropenylphenol and the second solvent is dl-lactic acid; the first solvent is n-butyl salicylate and the second solvent is dl-lactic acid or ethylene glycol; the first solvent is peony alcohol and the second solvent is dl-lactic acid; or the first solvent is thymol and the second solvent is 2,3-butanediol, 2-methyl-1,3-butanediol, or 2-hydroxy-2-methylpropanoic acid.

In Example 33, the composition of either of Examples 31 or 32, wherein the second solvent is dl-lactic acid and the first solvent is one of (E)-cinnamyl alcohol, 2-allylphenol, 4-propylphenol, chavicol, dihydroeugenol, hawthorn carbinol, hawthorn ethanol, isopropenylphenol, n-butyl salicylate, peony alcohol, and trans anethole.

In Example 34, the composition of any of Examples 31-33 wherein at least one of the first solvent and the second solvent has a Hansen polar solubility parameter of at least about 5.6 MPa$^{0.5}$, and a Hansen hydrogen bonding parameter of at least about 4.6 MPa$^{0.5}$.

In Example 35, the composition of any of Examples 31-34, wherein poly(ethylene terephthalate) is in solution with the first solvent and the second solvent in an amount no less than about 10 wt. %.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Poly(ethylene terephthalate) (PET) is a thermoplastic homopolymer of ethylene terephthalate monomer according to Formula I:

Formula I:

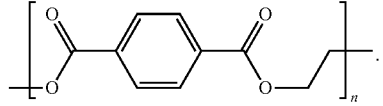

Solvents conventionally used to dissolve PET include 1,1,1,3,3,3-hexafluoroisopropanol, trifluoroacetic acid, trichloroacetic acid, phenol, chlorophenol, m-Cresol, and concentrated sulfuric acid. Each of these conventional solvents may be acutely hazardous to humans, the environment, or both. None of these conventional solvents would be desirable in the solvent processing of PET for used in implantable medical devices where residual amounts from the PET may end up in the body.

Embodiments of this disclosure employ a solvent mixture of two or more solvent components able to dissolve PET to form solutions of at least 2 weight percent (wt. %). PET. The solvent components may be less hazardous to humans and the environment than the conventional PET solvents described above. Individual solvent components may be homogeneous organic solvents, for example, dl-lactic acid or 2-allylphenol. Together, the solvent components of the solvent mixture dissolve PET. That is, the dissolved PET in the solvent mixture is no longer in solid form and does not settle out over a period of several days at room temperature (20° C. to 25° C.). The dissolved PET retains its basic polymer structure. That is, the number average molecular weight of the dissolved PET in the solvent mixture is within about 20% of the number average molecular weight of the PET when dissolved in 1,1,1,3,3,3-hexafluoroisopropanol.

Hansen Solubility Parameters (HSPs) may be used to predict whether a material may dissolve in another. HSPs consist of three parameters representing forces acting between molecules of a substance: dispersion forces, polar intermolecular forces, and hydrogen bonding forces (see Charles M. Hansen, *Hansen Solubility Parameters: A User's Handbook* (CRC Press, 2d ed. 2007)). The three HSPs define a three-dimensional Hansen space. The three HSPs of a material are coordinates in the Hansen space. Thus, the HSPs of a material, such as a solvent or polymer, determine relative position of the material in the Hansen space. The HSPs of a solvent mixture are a volume-weighted combination of the HSPs of the individual component solvents making up the solvent mixture. Thus, a solvent mixture also has a relative position in Hansen space. A Hansen Solubility Parameter Distance (Ra) is a distance in Hansen space between any two materials, such as a solvent mixture, a solvent component of a solvent mixture, or a polymer. The Ra may be determined from Equation 1:

$$Ra=\sqrt{4(\delta_{d2}-\delta_{d1})^2+(\delta_{p2}-\delta_{p1})^2+(\delta_{h2}-\delta_{h1})^2},\qquad\text{Equation 1:}$$

where $\delta_{d1}$, $\delta_{p1}$, and $\delta_{h1}$ are the dispersion, polar, and hydrogen bonding HSPs, respectively, of one of the two of a solvent mixture, a solvent component of a solvent mixture, or a polymer; and $\delta_{d2}$, $\delta_{p2}$, and $\delta_{h2}$ are the dispersion, polar and hydrogen bonding HSPs of the other of the two of a solvent mixture, a solvent component of a solvent mixture, or a polymer. The values of the HSPs for a particular solvent component may be determined empirically or may be found in published tables. In embodiments of the present disclosure, HSPs for various solvent components may be found in, for example, Charles M. Hansen, *Hansen Solubility Parameters: A User's Handbook* (CRC Press, 2d ed. 2007) incorporated herein by reference in its entirety.

It was found that solvent mixtures having an Ra less than 2 from HSP coordinates having a dispersion HSP of 18.02 MPa$^{0.5}$, a polar HSP of 5.56 MPa$^{0.5}$, and a hydrogen bonding HSP of 14.27 MPa$^{0.5}$, successfully dissolved PET. In some embodiments, the Ra between the solvent mixture and the HSP coordinates having a dispersion HSP of 18.02 MPa$^{0.5}$, a polar HSP of 5.56 MPa$^{0.5}$, and a hydrogen bonding HSP of 14.27 MPa$^{0.5}$ may be less than about 2.0 MPa$^{0.5}$, less than about 1.5 MPa$^{0.5}$, less than about 1.0 MPa$^{0.5}$, or less than about 0.5 MPa$^{0.5}$.

A solution including PET may be made by dissolving the PET in a solvent mixture consisting of two solvent components, a first solvent component and a second solvent component. In some embodiments, the first solvent component can be n-butyl salicylate and the second solvent component can be ethylene glycol. In other embodiments, the first solvent component can be benzyl alcohol and the second solvent component can be one of 1-butanol, iso-butanol, and ethylene glycol. In still other embodiments, the first solvent component can be thymol and the second solvent component can be one of 2,3-butanediol, 2-hydroxy-2-methylpropanoic acid, and 2-methyl-1,3-butanediol. In some embodiments, the first solvent component can be cinnamyl alcohol and the second solvent component can be one of 2-methyl-1,3-butanediol, 1-butanol, 2-propanol, or 3-methyl allyl alcohol.

In some embodiments, the second solvent component can be dl-lactic acid and the first solvent component can be one of (E)-cinnamyl alcohol, 2-allylphenol, 4-propylphenol, chavicol, dihydroeugenol, hawthorn carbinol, hawthorn ethanol, isopropenylphenol, n-butyl salicylate, peony alcohol, and trans anethole.

In some embodiments, the first solvent component may be present in concentrations of greater than or equal to about 50 vol. %, with the balance being the second solvent component. In some embodiments, a volume ratio of the first solvent to the second solvent may be 50% to 50%, 60% to 40%, 70% to 30%, 80% to 20%, 90% to 10%, or 95% to 5%, or any volume ratio between any of the preceding volume ratios.

In some embodiments, the solubility of the PET in the solvent mixture may be at least as great as about 2 wt. %, about 4 wt. %, about 6 wt. %, or about 8 wt. %, or may be no greater than about 12 wt. %, about 15 wt. %, about 18 wt. %, or about 20 wt. %, or may be present within any range defined between any pair of the foregoing values. For example, in some embodiments, the solubility of the PET in the solvent mixture may be in an amount from about 2 wt. % to about 20 wt. %, from about 4 wt. % to about 18 wt. %, from about 6% to about 15%, or from about 8 wt. % to about 12 wt. %. All solubility values described herein are at a temperature of room temperature (20° C. to 25° C.).

In some embodiments, at least one of the solvent components of the solvent mixture may have a polar HSP of at least about 5.6 MPa$^{0.5}$ and at least one of the solvent components may have a hydrogen bonding HSP of at least about 4.6 MPa$^{0.5}$. Including solvent components having a polar HSP of at least about 5.6 MPa$^{0.5}$ and a hydrogen bonding HSP of at least about 4.6 MPa0.5 may improve the efficiency by which the solution including the PET may be employed in some solvent-based processing such as, for example, electrospinning or electrospraying.

In another embodiment, an implantable medical device including a PET layer may be made by formulating a PET solution as described above, depositing the PET solution onto the implantable medical device, and drying the implantable device and evaporating the solvent mixture to leave behind the PET layer. In some embodiments, depositing the PET solution onto the implantable medical device may include at least one of solvent casting, spray coating, or dip coating of the PET solution onto the implantable medical device. In other embodiments, depositing the PET solution onto the implantable medical device may include at least one of electrospinning and electrospraying the PET solution onto the implantable medical device.

In some embodiments, drying the implantable medical device after deposition can include evaporating the solvent mixture at an elevated temperature and/or to leave behind the PET layer. In other embodiments, drying the implantable medical device after deposition can include evaporating the solvent mixture under a partial vacuum. In some embodiments, both an elevated temperature and a partial vacuum may be employed to dry the implantable medical device.

In yet another embodiment, a composition can include a first solvent, a second solvent, and PET in solution with the first solvent and the second solvent in an amount no less than about 2 wt. %, about 4 wt. %, about 6 wt. %, or about 8 wt. %, or may be no greater than about 12 wt. %, about 15 wt. %, about 18 wt. %, or about 20 wt. %, or may be present within any range defined between any pair of the foregoing values. For example, in some embodiments, the PET can be in the solution in an amount from about 2 wt. % to about 20 wt. %, from about 4 wt. % to about 18 wt. %, from about 6% to about 15%, or from about 8 wt. % to about 12 wt. %.

In some embodiments, the first solvent of the composition can be (E)-cinnamyl alcohol and the second solvent can be dl-lactic acid; the first solvent can be 2-allylphenol and the second solvent can be dl-lactic acid; the first solvent can be 4-propylphenol and the second can be dl-lactic acid; the first solvent can be trans anethole and the second solvent can be dl-lactic acid; the first solvent can be benzyl alcohol and the second solvent can be ethylene glycol, iso-butanol, or 1-butanol; the first solvent can be chavicol and the second solvent can be dl-lactic acid; the first solvent can be cinnamyl alcohol and the second solvent can be 2-methyl-1,3-butanediol, 1-butanol, 2-propanol, or 3-methyl allyl alcohol; the first solvent can be dihydroeugenol and the second solvent can be dl-lactic acid; the first solvent can be hawthorn carbinol, and the second solvent can be dl-lactic acid; the first solvent can be hawthorn ethanol and the second solvent can be dl-lactic acid; the first solvent can be isopropenylphenol and the second solvent can be dl-lactic acid; the first solvent can be n-butyl salicylate and the second solvent can be dl-lactic acid or ethylene glycol; the first solvent can be peony alcohol and the second solvent can be dl-lactic acid; or the first solvent can be thymol and the second solvent can be 2,3-butanediol, 2-methyl-1,3-butanediol, or 2-hydroxy-2-methylpropanoic acid.

In some embodiments, the first solvent may be present in concentrations of greater than or equal to about 50 vol. %, with the balance being the second solvent. In some embodiments, a volume ratio of the first solvent to the second solvent may be 50% to 50%, 60% to 40%, 70% to 30%, 80% to 20%, 90% to 10%, or 95% to 5%, or any volume ratio between any of the preceding volume ratios.

EXAMPLES

The present invention is more particularly described in the following examples that are intended as illustrations only, since numerous modifications and variations within the scope of the present invention will be apparent to those of skill in the art. Unless otherwise noted, all parts, percentages, and ratios reported in the following examples are on a weight bases, and all reagents used in the examples were obtained, or are available, from the chemical suppliers described below, or may be synthesized by conventional techniques.

Example 1

Poly(Ethylene Terephthalate) in 2-Phenoxy Ethanol and Thymol

Poly(ethylene terephthalate) (PET) was obtained from Sigma Aldrich® (CAS #25038-59-9) in the form of 3-5 mm diameter pellets. 1.1 g of PET was added to a solvent mixture of 10 ml of 2-phenoxy ethanol (CAS #122-99-6) and 0.638 ml of thymol (CAS #89-83-8). The PET and solvent mixture was heated to about 120° C. and stirred for about 12 hours. The PET was observed to dissolve in the solvent mixture. The resulting PET solution was allowed to cool to room temperature. After 24 hours, no precipitate was observed in the PET solution, which contained about 8.6 wt. % PET.

Example 2

Poly(Ethylene Terephthalate) in Thymol and 2-Methyl-1,3-Butanediol

Poly(ethylene terephthalate) (PET) as described above for Example 1 in the amount of 0.65 g was added to a solvent mixture of 12 ml of thymol and 0.638 ml of 2-methyl-1,3-butanediol (CAS #684-84-4). The PET and solvent mixture was heated to about 80° C. and stirred for about 12 hours. The PET was observed to dissolve in the solvent mixture. The resulting PET solution was allowed to cool to room temperature. After 24 hours, no precipitate was observed in the PET solution, which contained about 5.0 wt. % PET.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:
1. A composition comprising:
a first solvent;
a second solvent; and
poly(ethylene terephthalate) in solution with the first solvent and the second solvent in an amount no less than about 2 wt. %,
wherein a Hansen Solubility Parameter Distance between the solvent mixture and HSP coordinates having a dispersion HSP of 18.02 MPa$^{0.5}$, a polar HSP of 5.56 MPa$^{0.5}$, and a hydrogen bonding HSP of 14.27 MPa$^{0.5}$ is less than about 2 MPa$^{0.5}$, and
wherein the first solvent of the composition is (E)-cinnamyl alcohol and the second solvent is dl-lactic acid; the first solvent is 2-phenoxy ethanol and the second solvent is thymol; the first solvent is 2-allylphenol and the second solvent is dl-lactic acid; the first solvent cis 4-propylphenol and the second is dl-lactic acid; the first solvent is trans anethole and the second solvent is dl-lactic acid; the first solvent is benzyl alcohol and the second solvent is ethylene glycol, iso-butanol, or 1-butanol; the first solvent is chavicol and the second solvent is dl-lactic acid; the first solvent is cinnamyl alcohol and the second solvent is 2-methyl-1,3-butanediol, 1-butanol, 2-propanol, or 3-methyl allyl alcohol; the first solvent is dihydroeugenol and the second solvent is dl-lactic acid; the first solvent is hawthorn carbinol, and the second solvent is dl-lactic acid; the first solvent is hawthorn ethanol and the second solvent is dl-lactic acid; the first solvent is isopropenylphenol and the second solvent is dl-lactic acid; the first solvent is n-butyl salicylate and the second solvent is dl-lactic acid or ethylene glycol; the first solvent is peony alcohol and the second solvent is dl-lactic acid; or the first solvent is thymol and the second solvent is 2,3-butanediol, 2-methyl-1,3-butanediol, or 2-hydroxy-2-methylpropanoic acid.

2. The composition of claim 1, wherein the second solvent is dl-lactic acid and the first solvent is one of (E)-cinnamyl alcohol, 2-allylphenol, 4-propylphenol, chavicol, dihydroeugenol, hawthorn carbinol, hawthorn ethanol, isopropenylphenol, n-butyl salicylate, peony alcohol, and trans anethole.

3. The composition of claim 1, wherein the first solvent is 2-phenoxy ethanol and the second solvent is thymol; or the first solvent is n-butyl salicylate and the second solvent is ethylene glycol.

4. The composition of claim 1, wherein the first solvent is benzyl alcohol and the second solvent is one of 1-butanol, iso-butanol, and ethylene glycol.

5. The composition of claim 1, wherein the first solvent component is thymol and the second solvent component is one of 2,3-butanediol, 2-hydroxy-2-methylpropanoic acid, and 2-methyl-1,3-butanediol.

6. The composition of claim 1, wherein the first solvent component is cinnamyl alcohol and the second solvent component is one of 2-methyl-1,3-butanediol, 1-butanol, 2-propanol, or 3-methyl allyl alcohol.

7. The composition of claim 1, wherein at least one of the first solvent and the second solvent has a Hansen polar solubility parameter of at least about 5.6 MPa$^{0.5}$, and a Hansen hydrogen bonding parameter of at least about 4.6 MPa$^{0.5}$.

8. The composition of claim 1, wherein the poly(ethylene terephthalate) is in solution with the first solvent and the second solvent in an amount no less than about 10 wt. %.

9. The composition of claim 1, wherein the poly(ethylene terephthalate) is in solution with the first solvent and the second solvent in an amount from about 4 wt. % to about 18 wt. %.

10. A composition comprising:
a first solvent;
a second solvent; and
poly(ethylene terephthalate) in solution with the first solvent and the second solvent in an amount no less than about 2 wt. %, wherein a Hansen Solubility Parameter Distance between the solvent mixture and HSP coordinates having a dispersion HSP of 18.02 MPa$^{0.5}$, a polar HSP of 5.56 MPa$^{0.5}$, and a hydrogen bonding HSP of 14.27 MPa$^{0.5}$ is less than about 2 MPa$^{0.5}$, wherein the first solvent of the composition is (E)-cinnamyl alcohol and the second solvent is dl-lactic acid; the first solvent is 2-phenoxy ethanol and the second solvent is thymol; the first solvent is 2-allylphenol and the second solvent is dl-lactic acid; the first solvent cis 4-propylphenol and the second is dl-lactic acid; the first solvent is trans anethole and the second solvent is dl-lactic acid; the first solvent is benzyl alcohol and the second solvent is ethylene glycol, iso-butanol, or 1-butanol; the first solvent is chavicol and the second solvent is dl-lactic acid; the first solvent is cinnamyl alcohol and the second solvent is 2-methyl-1,3-butanediol, 1-butanol, 2-propanol, or 3-methyl allyl alcohol; the first solvent is dihydroeugenol and the second solvent is dl-lactic acid; the first solvent is hawthorn carbinol, and the second solvent is dl-lactic acid; the first solvent is hawthorn ethanol and the second solvent is dl-lactic acid; the first solvent is isopropenylphenol and the second solvent is dl-lactic acid; the first solvent is n-butyl salicylate and the second solvent is dl-lactic acid or ethylene glycol; the first solvent is peony alcohol and the second solvent is dl-lactic acid; or the first solvent is thymol and the second solvent is 2,3-butanediol, 2-methyl-1,3-butanediol, or 2-hydroxy-2-methylpropanoic acid.

11. The composition of claim 10, wherein the second solvent is dl-lactic acid and the first solvent is one of (E)-cinnamyl alcohol, 2-allylphenol, 4-propylphenol, chavicol, dihydroeugenol, hawthorn carbinol, hawthorn ethanol, isopropenylphenol, n-butyl salicylate, peony alcohol, and trans anethole.

12. The composition of claim 10, wherein at least one of the first solvent and the second solvent has a Hansen polar solubility parameter of at least about 5.6 MPa$^{0.5}$, and a Hansen hydrogen bonding parameter of at least about 4.6 MPa$^{0.5}$.

13. The composition of claim 10, wherein the first solvent is 2-phenoxy ethanol and the second solvent is thymol; or the first solvent is n-butyl salicylate and the second solvent is ethylene glycol.

14. The composition of claim 10, wherein the first solvent is benzyl alcohol and the second solvent is one of 1-butanol, iso-butanol, and ethylene glycol.

15. The composition of claim 10, wherein the first solvent component is thymol and the second solvent component is one of 2,3-butanediol, 2-hydroxy-2-methylpropanoic acid, and 2-methyl-1,3-butanediol.

16. The composition of claim 10, wherein the first solvent component is cinnamyl alcohol and the second solvent component is one of 2-methyl-1,3-butanediol, 1-butanol, 2-propanol, or 3-methyl allyl alcohol.

17. The composition of claim 10, wherein the poly(ethylene terephthalate) is in solution with the first solvent and the second solvent in an amount no less than about 10 wt. %.

18. The composition of claim 1, wherein the poly(ethylene terephthalate) is in solution with the first solvent and the second solvent in an amount from about 4 wt. % to about 18 wt. %.

* * * * *